(12) United States Patent
Chao et al.

(10) Patent No.: US 9,133,106 B2
(45) Date of Patent: Sep. 15, 2015

(54) METHOD FOR PRODUCING KETOXIME

(71) Applicant: China Petrochemical Development Corporation, Taipei (Taiwan), Taipei (TW)

(72) Inventors: Shih-Yao Chao, Taipei (TW); Cheng-Fa Hsieh, Taipei (TW); Chien-Chang Chiang, Taipei (TW); Pin-To Yao, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 106 days.

(21) Appl. No.: 14/087,511

(22) Filed: Nov. 22, 2013

(65) Prior Publication Data

US 2014/0179951 A1 Jun. 26, 2014

(30) Foreign Application Priority Data

Dec. 25, 2012 (TW) .............................. 101149709 A

(51) Int. Cl.
*C07C 249/04* (2006.01)

(52) U.S. Cl.
CPC .................................. *C07C 249/04* (2013.01)

(58) Field of Classification Search
None
See application file for complete search history.

(56) References Cited

U.S. PATENT DOCUMENTS

| | | |
|---|---|---|
| 4,410,501 A | 10/1983 | Taramasso et al. |
| 4,968,842 A | 11/1990 | Padovan et al. |
| 5,227,525 A | 7/1993 | Tonti et al. |
| 5,312,987 A | 5/1994 | Mantegazza et al. |
| 6,828,459 B2 | 12/2004 | Oikawa et al. |

FOREIGN PATENT DOCUMENTS

| | | |
|---|---|---|
| CN | 1706818 A | 12/2005 |
| CN | 101318912 A | 12/2008 |
| CN | 101544582 A | 9/2009 |
| EP | 0347926 | * 12/1989 |

* cited by examiner

*Primary Examiner* — Rosalynd Keys
*Assistant Examiner* — Jennifer C Sawyer
(74) *Attorney, Agent, or Firm* — Mintz Levin Cohn Ferris Glovsky and Popeo, P.C.; Peter F. Corless; Steven M. Jensen

(57) ABSTRACT

A method for producing a ketoxime is provided. The method includes the step of performing a reaction of a nitrogen-containing compound, ketone and an oxidant by using a titanium-silicon molecular sieve as a catalyst, so as to form the ketoxime, thereby increasing the yield and selectivity of the ketoxime.

11 Claims, No Drawings

METHOD FOR PRODUCING KETOXIME

CROSS-REFERENCES TO RELATED APPLICATIONS

This application claims under 35 U.S.C. §119(a) the benefit of Taiwanese Application No. 101149709, filed Dec. 25, 2012, the entire contents of which is incorporated herein by reference.

FIELD OF THE INVENTION

The present invention relates to methods for producing ketoximes, and relates particularly to a process for producing a ketoxime by using a magnesium-containing titanium-silicon molecular sieve as a catalyst.

BACKGROUND OF RELATED ART

Butanone oxime is often used industrially as an anti-skinning agent or an oxygen scavenger in paints, and can be further used for producing methyltributanoneoximido silane or vinyltributanoneoximido silane which is used as a neutral cross-linking agent or a silicon rubber-based sealing agent. These chemical raw materials have a wide variety of applications in architectures, automobiles and pharmaceuticals.

Generally, a hydroxyl ammonium method is mainly used for producing butanone oxime. This method involves reacting butanone and acidic hydroxyl ammonium to produce butanone oxime. However, this method not only has complex steps and high equipment cost, but also produces a large amount of low-valued ammonium salts as byproducts which are detrimental to the environment. Therefore, in order to avoid harming the environment, a crystalline titanium-silicon molecular sieve (also referred to as "TS-1" molecular sieve) with an MFI structure is obtained by introducing a titanium atom into a silica network structure. The TS-1 molecular sieve is used to catalyze oxidation, such as hydroxylation of aromatic hydrocarbons, ammoxidation of alkenes, partial oxidation of alkanes, and ammoxidation of ketones, to bring about significant catalytic activities and selectivity of products.

As to ammoxidations of ketones, cyclic ketones or linear ketones can usually be selected as raw materials for reactions, U.S. Pat. No. 4,410,501, U.S. Pat. No. 4,968,842, U.S. Pat. No. 5,227,525, U.S. Pat. No. 5,312,987 and U.S. Pat. No. 6,828,459 disclose ammoxidation performed by using cyclic ketones. However, there are very few literatures related to ammoxidation of linear ketones. Chinese Patent No. 1706818 and Chinese Patent No. 101318912 disclose the uses of a TS-1 molecular sieve to catalyze oxidation to prepare linear ketoximes. Nevertheless, yields of ketoximes in these patents are poor.

Moreover, Chinese Patent No. 101544582 also discloses a method for preparing butanone oxime, which involves adding a noble metal to modify a TS-1 catalyst for the use in ammoxidation of butanone. The selectivity of butanone oxime significantly increases to 90%. However, the conversion rate of butanone is at most 10%.

Accordingly, there is a need to develop a process for preparing a ketoxime with high product selectivity, high conversion rates of the raw materials, and high yield of ketoximes.

SUMMARY OF THE INVENTION

The present invention provides a method for preparing a ketoxime, which includes the step of performing a reaction of a nitrogen-containing compound, ketone and an oxidant by using a titanium-silicon molecular sieve of formula (I) as a catalyst, so as to form the ketoxime. Formula (I) is as follows:

$$(Mg_x Ti_y Si)O_z \qquad (I)$$

wherein x is in a range of from 0.0001 to 0.02, y is in a range of from 0.001 to 0.07, and z is x+2y+2.

In an embodiment, the titanium-silicon molecular sieve has a structure selected from the group consisting of MFI, MEL, BEA, ZSM-48, MTW or MCM-41 structures.

In the aforesaid method, a molar ratio of the oxidant to the ketone is in a range of from 0.8:1 to 2.5:1, and preferably of from 1.0:1 to 1.5:1. The molar ratio of the nitrogen-containing compound to the ketone is in a range from 1:1 to 5:1, and preferably from 1.2:1 to 2.0:1.

In the method of the present invention, the temperature at which the reaction is performed is not particularly limited. The temperature may be in a range of from 0 to 150° C., and preferably from 20 to 120° C.

In the method of the present invention, the oxidant is hydrogen peroxide.

In the aforesaid method, the oxidant is fed into a reaction system as the progression of the reaction time. The retention time of the oxidant in the reaction is from 30 minutes to 2 hours, and preferably 1 hour.

The method of present invention can be performed under any pressure (but preferably from 0.1 to 11 atmospheric pressures (atm)), so as to increase the solubility of the gaseous reactants.

In the method of the present invention, the amount of the catalyst is not strictly limited, as long as the amount of the catalyst can allow the completion of ammoxidation within the shortest time.

In the method of the present invention, the reaction is performed in the presence of a solvent. In the aforesaid method, the solvent may be, but not limited to, water, $C_1$-$C_5$ alcohol or as combination thereof.

In the aforesaid method, the method of the present invention involves ammoxidation by a batch-type approach. Usually, the amount of the catalyst is in a range of from 0.1 to 20 wt %, based on the total weight of the nitrogen-containing compounds, the ketone, the solvent and the oxidant.

In the method of the present invention, the reaction may be performed in any suitable reaction vessel or apparatus, such as a fixed bed, transport bed, fluidized bed, stirred slurry, or continuous flow stirred reactor by a batch-type, continuous-type or semi-continuous type approach in a single-phase or two-phase system.

The method of the present invention has a simple process, high conversion rates of the raw materials, and high product selectivity, and is indeed suitable for industrial uses.

DETAILED DESCRIPTION OF THE PREFERRED EMBODIMENTS

In the following, specific embodiments are provided to illustrate the detailed description of the present invention. Those skilled in the art can easily conceive the advantages and effects of the present invention, based on the disclosure of the specification. The present invention can also be practiced or applied by referring to the other different embodiments. Each of the details in the specification can also be modified or altered in various ways in view of different aspects and applications, without departing from the spirit of the disclosure of the present invention.

The titanium-silicon molecular sieve used in the method of the present invention, in an anhydrous state, has the following chemical formula:

$$(Mg_xTi_ySi)O_z \qquad (I)$$

wherein x is in a range of from 0.0001 to 0.02, y is in a range of from 0.001 to 0.07, and z is x+2y+2.

The titanium-silicon molecular sieve may be powdery, bulky, microspherical, monolithic, extrusion molded or in any other forms.

In order to obtain the titanium-silicon molecular sieve, the present invention further discloses a method for preparing a titanium-silicon molecular sieve. The method includes the steps of thoroughly mixing a silicon source, a titanium source, a source of an alkaline earth metal and a template agent in alkaline condition to form a mixture, and then heating the mixture to obtain a mixed gel; performing a hydrothermal reaction on the mixed gel at 100 to 200° C. (preferably from 140 to 185° C.) for 1 hour to 10 days (preferably from 6 hours to 3 days); and sintering the mixed gel which contains the alkaline earth metal and underwent the hydrothermal reaction, for 0.5 to 24 hours to obtain a titanium-silicon molecular sieve.

Moreover, the method for producing a solid catalyst in the present invention may further include the steps of adding a dispersion into the mixed gel after the mixed gel is formed, and performing a hydrothermal treatment on the mixed gel containing the dispersion, wherein the dispersion includes water and a silica sol.

Crystals of a titanium-silicon molecular sieve obtained by the hydrothermal reaction can be isolated from the reaction solution by any suitable conventional method, which may be filtration, centrifugation, decantation or other similar approaches.

The silicon source used in the method for preparing a titanium-silicon molecular sieve of the present invention, may be, but not limited to, fumed silicon (silica), silica gel, silica sol, tetraalkyl silicate (such as tetramethyl silicate, tetraethyl silicate, tetrapropyl silicate and tetrabutyl silicate). Examples of silica sol includes Ludox AS-40, Ludox AS-30, Ludox AM-30, Ludox TM-40, Ludox TM-50, Ludox AM-30, Ludox HS-30 and Ludox HS-40 manufactured by DuPont, or SNOWTEX-40, SNOWTEX-50, SNOWTEX-C, SNOWTEX-N, SNOWTEX-20L, SNOWTEX-ZL and SNOWTEX-UP manufactured by Nissan Chemical, or other similar products.

The titanium source used in the method for producing a titanium-silicon molecular sieve in the present invention may be, but not limited to, a titanium salt (such as titanium halide), or tetraalkyl titanate. The titanium sources used in preferred embodiments may be, but not limited to, tetramethyl titanate, tetraethyl titanate, tetrapropyl n-titanate, tetrabutyl n-titanate, tetra-sec-butyl titanate, tetrabutyl isotitanate, tetra-t-butyl titanate or a combination thereof.

The source of an alkaline earth metal used in the method for producing a titanium-silicon molecular sieve of the present invention is a magnesium source, such as magnesium alkoxide or magnesium salts; for example, magnesium halide, magnesium hydroxide, magnesium carbonate, magnesium phosphate, magnesium sulfate, magnesium nitrate, magnesium acetate and magnesium silicate.

The template agent used in the method for producing a titanium-silicon molecular sieve of the present invention may be, but not limited to, an aqueous solution or an alcohol solution of a nitrogen-containing organic alkaline substance, wherein the nitrogen-containing organic alkaline substance is at a concentration of from 5 to 50 wt %, and preferably from 20 to 40 wt %. In the embodiments, the nitrogen-containing organic alkaline substance used in the method for producing a titanium-silicon molecular sieve of the present invention may be, hut not limited to, alkylammonium hydroxide, such as tetra-n-propylammonium hydroxide, and tetra-n-butylammonium hydroxide; alkylammonium halide, such as an aqueous solution or alcohol solution of tetra-n-propylammonium bromide, and tetra-n-butylammonium bromide; an organic amine, such as triethylamine and ethyldiamine, "Alcohol" in the alcohol solution refers to an alcohol having 1 to 5 carbon atoms, such as methanol, ethanol, isopropanol, n-butanol and t-butanol. The solvent can accelerate the formation of crystals of a titanium-silicon molecular sieve.

In the method for forming a titanium-silicon molecular sieve of the present invention, a molar ratio of the nitrogen-containing organic alkaline substance to the silicon in the mixed gel is in a range of from 0.1 to 5, preferably from 0.15 to 0.45, and more preferably from 0.2 to 0.4.

The structure of the nitrogen-containing organic alkaline substance can be altered to control the configuration of the titanium-silicon molecular sieve, such as MFI (ZSM-5), MEL (ZSM-11), BEA (beta), ZSM-48, MTW (ZSM-12), MCM-41 or other predetermined configurations. For example, tetra-n-propylammonium hydroxide can render an MFI configuration of the titanium-silicon molecular sieve, in any of the configurations, titanium atoms are introduced into the silica network structures to form active sites.

Furthermore, in the titanium-silicon molecular sieve of the present invention, other transitional metals can be optionally further incorporated by an immersion method, precipitation method, a blending method or other similar methods, if it is necessary. In the immersion method, a solution of transitional metals is dispersed into an appropriate solvent, and then mixed with a molecular sieve to form a titanium-silicon molecular sieve impregnated with the transitional metals. Optionally, depending on the needs, the titanium-silicon molecular sieve impregnated with the transitional metals is further dried and sintered, wherein the transitional metals are at concentrations ranging from 0.01 to 10 weight percents (wt %), and preferably from 0.05 to 5 wt %, based on the total weight of the titanium-silicon molecular sieve of the present invention. Regarding the titanium-silicon molecular sieve impregnated with the transitional metals as prepared by the immersion method, the transitional metals are located within or outside the backbone of the titanium-silicon molecular sieve. When the titanium-silicon molecular sieve impregnated with the transitional metals is used as a catalyst in ammoxidation, all or some of the transitional metals undergo reduction.

In the method for preparing a ketoxime of the present invention, the nitrogen-containing compound used may be, but not limited to, ammonium hydroxide or ammonia.

The oxidant used in the method for preparing a ketoxime of the present invention is hydrogen peroxide ($H_2O$), but may be various compounds which are capable of generating or releasing hydrogen peroxide.

When the titanium-silicon molecular sieve impregnated with the transitional metals is used as a catalyst, hydrogen peroxide used in the method of the present invention can be formed hi-situ. For example, hydrogen and oxygen gases are introduced into an ammoxidating reactor containing the titanium-silicon molecular sieve impregnated with the transitional metals (such as palladium and platinum), so a to generate hydrogen peroxide.

In the method for preparing a ketoxime of the present invention, an additional solvent may be optionally added to dissolve reactants (such as a nitrogen-containing compound, ketone and oxidant) other than the titanium-silicon molecular sieve, and to provide a better temperature control to increase the reaction rate and selectivity of ammoxidation, wherein the amount of the solvent is in a range of from 1 to 99 wt % of the mixture in ammoxidation based on the total weight of the mixture in ammoxidation. Further, the solvent is in a liquid state at the temperature of ammoxidation.

In the method for preparing a ketoxime of the present invention, the solvent may be, but not limited to, alcohols or water. The presence of water does not have a significant adverse impact on ammoxidation.

The present invention is further illustrated in, but not limited to, the following examples. Those skilled in the art can conceive the other advantages and effects of the present invention, based on the disclosure of the specification.

Comparative Example 1

A 500 mL round-bottomed flask was sealed with nitrogen in a vacuum system. Thirty grams (g) of tetraethyl silicate and 56 g (20 wt %) of an isopropanol solution of tetra-n-propyl ammonium hydroxide were added to the round-bottomed flask, and continuously stirred at 5° C. After the temperature reached a balance, 1.467 g of tetra-n-butyl titanate was added to the round-bottomed flask, and continuously stirred for 1 hour. Then, 44.8 g of water was slowly added spanning 1.5 hour through an isobaric feeding-tube, and then stirred for 1 hour, such that a gel mixture was obtained. Alcohol was then removed from the gel mixture at 85° C. for 2 hours. At the same time, a dispersion was prepared by dispersing 10.8 g of silica sol solution (DuPont; Ludox AS-40) in 73.5 g of water. The dispersion was added to the gel mixture after the alcohol contained in the gel mixture was removed, and then the mixture was stirred for 1 hour. The mixture containing the gel mixture without alcohol contained therein and the dispersion was sealed in a pressure-resistant stainless-steel tank lined with Teflon, and subjected to a hydrothermal reaction at 180° C. for 120 hours. The solid and liquid were separated. The solid was washed with water until being neutral, dried at 100° C., and sintered at 550° C. for 8 hours to obtain a titanium-silicon molecular sieve of comparative example 1.
Preparation of a titanium-silicon molecular sieve of the present invention $$(Mg_xTi_ySi)O_z \qquad (I)$$

Example 1

A 500 mL round-bottomed flask was sealed with nitrogen in a vacuum system. Thirty grams of tetraethyl silicate and 56 g (20 wt %) of an isopropanol solution of tetra-n-propyl ammonium hydroxide were added to the round-bottomed flask, and continuously stirred at 5° C. After the temperature reached a balance, 1.467 g of tetra-n-butyl titanate was added to the round-bottomed flask, and continuously stirred for 1 hour. Then, 0.1331 g of magnesium sulfate ($MgSO_4 \cdot 7H_2O$) and 44.8 g of water were thoroughly mixed. The magnesium sulfate solution was added gradually to the round-bottomed flask spanning 1.5 hour by using an isobaric feeding-tube, and then stirred for 1 hour to obtain a gel mixture. Alcohol in the gel mixture was subsequently removed at 85° C. for 2 hours. At the same time, a dispersion was prepared by dispersing 21.60 g of silica sol solution (DuPont; Ludox AS-40) in 147 g of water. The dispersion was added to the gel mixture without alcohol contained therein, and the mixture was stirred for 1 hour. The mixture containing the gel mixture without alcohol contained therein and the dispersion was sealed in a pressure-resistant stainless-steel tank lined with Teflon, and subjected to a hydrothermal reaction at 180° C. for 120 hours. The solid and liquid were separated. The solid was washed with water until being neutral, dried at 100° C., and sintered at 550° C. for 8 hours to obtain a titanium-silicon molecular sieve of the present invention (example 1), which has a chemical formula (I) in an anhydrous state, wherein x is 0.0025, y is 0.02, and z is 2.0425.

Examples 2 and 3

Examples 2 and 3 are similar to example 1 except that 0.2662 g of magnesium sulfate was used in example 2, and 0.3993 g of magnesium sulfate was used in example 3. The chemical formulae of the titanium-silicon molecular sieves of the present invention in anhydrous states, as prepared in examples 2 and 3, are shown in Table 1.

Example 4

A 500 mL round-bottomed flask was sealed with nitrogen in a vacuum system. Thirty grams of tetraethyl silicate and 56 g (20 wt %) of an isopropanol solution of tetra-n-propyl ammonium hydroxide were added to the round-bottomed flask, and continuously stirred at 5° C. After the temperature reached a balance, 1.98 g of tetra-n-butyl titanate was added to the round-bottomed flask, and continuously stirred for 1 hour. Then, 0.1331 g of magnesium sulfate ($MgSO_4 \cdot 7H_2O$) and 44.8 g of water were thoroughly mixed. The magnesium solution was gradually added to the round-bottomed flask spanning 1.5 hour by using an isobaric feeding-tube, and then stirred for 1 hour to obtain a gel mixture. Alcohol in the gel mixture was then removed at 85° C. for 2 hours. At the same time, a dispersion was prepared by dispersing 21.60 g of silica sol solution (DuPont; Ludox AS-40) in 147 g of water. The dispersion was added to the gel mixture without alcohol contained therein, and then the mixture was stirred for 1 hour. The mixture containing the gel mixture without alcohol contained therein and the dispersion was sealed in a pressure-resistant stainless-steel tank lined with Teflon, and subjected to a hydrothermal reaction at 180° C. for 120 hours. The solid and liquid were separated. The solid was washed with water until being neutral, dried at 100° C., and sintered at 550° C. for 8 hours to obtain a titanium-silicon molecular sieve of the present invention (example 4), which has a chemical formula (I) in an anhydrous state.

Examples 5 and 6

Examples 5 and 6 are similar to example 4 except that 0.2662 g of magnesium sulfate was used in example 5, and 0.3993 g of magnesium sulfate was used in example 6. The chemical formulae of the titanium-silicon molecular sieves of the present invention in anhydrous states, as prepared in examples 5 and 6, are shown in Table 1.

TABLE 1

|  | Chemical formula |
|---|---|
| Example 2 | $(Mg_{0.005}Ti_{0.02}Si)O_{2.045}$ |
| Example 3 | $(Mg_{0.0075}Ti_{0.02}Si)O_{2.0475}$ |
| Example 4 | $(Mg_{0.0025}Ti_{0.027}Si)O_{2.0565}$ |
| Example 5 | $(Mg_{0.005}Ti_{0.027}Si)O_{2.059}$ |
| Example 6 | $(Mg_{0.0075}Ti_{0.027}Si)O_{2.0615}$ |

Preparation of a Ketoxime

Examples 7 to 12

The titanium-silicon molecular sieves prepared in comparative example 1 and examples 1 to 6 were used as catalysts, respectively in the ammoxidation of butanone and ammonium hydroxide to generate butanone oxime. The ammoxidation is illustrated as follows.

1.1 g of a titanium-silicon molecular sieve, 3.68 g of butanone and 12.43 g of 28 wt % of an ammonium hydroxide solution were added into a three-necked flask, and thoroughly mixed. Then, under a closed condition, at an air pressure of 1 atmospheric pressure (atm) and a reaction temperature maintained at 60° C., 4.96 g of hydrogen peroxide (35 wt %) was added at a feeding rate of 1.0 mL per minute into the reaction system. An isobaric equipment was used to maintain the pressure at 1 atm. After the feeding of hydrogen peroxide was completed, the reaction was performed for 1 hour, and then the reaction fluid was removed. Each of the catalysts was separated from the reaction fluids. Each of the reaction fluids was analyzed by using gas chromatography and titrator.

The selectivity of butanone and the concentration of each product were analyzed by using gas chromatography and titrator. The results are shown in Table 2.

TABLE 2

| | | Ammoxidation of butanone | | | | |
|---|---|---|---|---|---|---|
| | Catalyst | $X_K$ (%) | $S_{OX}$ (%) | $X_H$ (%) | $S_H$ (%) | $Y_{OX}$ (%) |
| Example 7 | Comparative Example 1 | 97.93 | 89.76 | 99.82 | 87.98 | 87.90 |
| Example 8 | Example 1 | 97.03 | 94.84 | 99.73 | 92.18 | 92.02 |
| Example 9 | Example 2 | 96.38 | 96.05 | 99.78 | 92.85 | 92.57 |
| Example 10 | Example 3 | 97.96 | 94.71 | 99.80 | 92.93 | 92.78 |
| Example 11 | Example 4 | 98.35 | 94.53 | 99.93 | 93.24 | 92.97 |
| Example 12 | Example 5 | 97.46 | 96.09 | 99.75 | 93.90 | 93.65 |
| Example 13 | Example 6 | 97.55 | 93.07 | 99.33 | 91.50 | 90.79 |

$X_K$: conversion rate of butanone = number of moles of consumed butanone/number of moles of added butanone × 100%;
$S_{OX}$: selectivity of butanone oxime = number of moles of generated butanone oxime/number of moles of consumed butanone × 100%;
$X_H$: conversion rate of hydrogen peroxide = number of moles of consumed hydrogen peroxide/number of moles of added hydrogen peroxide × 100%;
$S_H$: selectivity of hydrogen peroxide = number of moles of generated butanone oxime/number of moles of consumed hydrogen peroxide × 100%; and
$Y_{OX}$: yield of butanone oxime = number of moles of generated butanone oxime/number of moles of added butanone × 100%.

As shown in Table 2, by using the magnesium-containing titanium-silicon molecular sieves of the present invention (examples 8 to 13) in the ammoxidation, the selectivity of butanone and hydrogen peroxide, and the yields of butanone oxime of the present invention were all superior than those in the ammoxidation by using a conventional titanium-silicon molecular sieve (example 7).

Moreover, as compared with example 7, when the amounts of magnesium ions added to the magnesium-containing titanium-silicon molecular sieves were lower (examples 8 and 11), the yields of butanone oxime were significantly increased by increasing the selectivity of butanone and hydrogen peroxide under the circumstance that the conversion rates of butanone and hydrogen peroxide were similar.

Furthermore, as compared with example 8, when the amounts of magnesium ions added to the magnesium-containing titanium-silicon molecular sieves in examples 9 and 10 of the present invention were increased, the conversion rates of hydrogen peroxide were increased.

As shown from the above examples, the method of the present invention is a simple process, and provides high selectivity of ketone and hydrogen peroxide and a high yield of ketoxime while maintaining higher conversion rates of ketones and hydrogen peroxide. Accordingly, the present invention indeed increases production benefits.

The above examples are only used to illustrate the principle of the present invention and the effect thereof, and should not be construed as to limit the present invention. The above examples can all be modified and altered by those skilled in the art, without departing from the spirit and scope of the present invention as defined in the following appended claims.

What is claimed is:

1. A method for producing a ketoxime, comprising:
performing a reaction of a nitrogen-containing compound, a ketone and an oxidant by using a titanium-silicon molecular sieve of formula (I) as a catalyst, so as to form the ketoxime, $$(Mg_xTi_ySi)O_z \qquad (I)$$

wherein x is in a range of from 0.0001 to 0.02, y is in a range of from 0.001 to 0.07, and z is x+2y+2.

2. The method of claim 1, wherein the titanium-silicon molecular sieve has a structure selected from the group consisting of MFI, MEL, BEA, ZSM-48, MTW and MCM-41 structures.

3. The method of claim 1, wherein a molar ratio of the oxidant to the ketone is in a range of from 0.8:1 to 2.5:1.

4. The method of claim 1, wherein a molar ratio of the nitrogen-containing compound to the ketone is in a range of from 1:1 to 5:1.

5. The method of claim 1, wherein the oxidant is hydrogen peroxide.

6. The method of claim 1, wherein the reaction is performed at a pressure in a range of from 0.1 to 11 atm.

7. The method of claim 1, wherein the reaction is performed at a temperature in a range of from 20 to 120° C.

8. The method of claim 1, wherein the reaction is performed in the presence of a solvent.

9. The method of claim 8, wherein an amount of the catalyst is in a range of from 0.1 to 20 wt % based on a total weight of the nitrogen-containing compound, the ketone, the solvent and the oxidant.

10. The method of claim 8, wherein the solvent is one selected from the group consisting of water, $C_1$-$C_5$ alcohol and a combination thereof.

11. The method of claim 1, wherein the nitrogen-containing compound is ammonium hydroxide or ammonia.

* * * * *